United States Patent [19]

Perkins et al.

[11] 4,446,578

[45] May 8, 1984

[54] JOINT TREATMENT

[76] Inventors: Ezra C. Perkins, 10950 Temple Ter., Apt. 719, Seminole, Fla. 33542; Ronald G. Connolly, 2401 Pennsylvania Ave., Wilmington, Del. 19806

[21] Appl. No.: 355,872

[22] Filed: Mar. 8, 1982

[51] Int. Cl.$^3$ .......................... A61F 1/24; A61F 1/00
[52] U.S. Cl. ..................................... 3/1.91; 128/1 R; 128/92 C; 128/DIG. 21
[58] Field of Search .................................. 3/1.9–1.913, 3/1; 128/92 C, 92 CA, 1 R, DIG. 21

[56] References Cited

U.S. PATENT DOCUMENTS

| Re. 29,345 | 8/1977 | Erb | 128/1 R |
|---|---|---|---|
| 3,805,767 | 4/1974 | Erb | 128/1 R |
| 3,879,767 | 4/1975 | Stubstad | 3/1.91 |
| 4,052,753 | 10/1977 | Dedo | 3/1.911 X |
| 4,085,466 | 4/1978 | Goodfellow et al. | 3/1.91 |
| 4,245,623 | 1/1981 | Erb | 128/1 R |
| 4,292,972 | 10/1981 | Pawelchak et al. | 128/156 X |
| 4,385,404 | 5/1983 | Sully et al. | 3/1.91 |

FOREIGN PATENT DOCUMENTS 2419065  11/1979  France .......................................... 3/1

OTHER PUBLICATIONS

"The Effect of Injected Silicones Upon the Tissues of Animals" by C. Nedelman, *The Bulletin* of the Dow Corning Center for Aid to Medical Research, vol. 12, No. 2, Jul. 1970, pp. 6–7.

McGhan Silicone Block Gel Elastomer, Advertisement McGhan Medical Corp., 700 Ward Dr., Santa Barbara, Ca., Feb. 1977 (2 pp.).

"The Bulletin", Jan. 1967–Title Page.

J. Pros. Dent., Jan. 1970–vol. 23, No. 1–C. I. Nedelman–pp. 25–35.

J. Reprod. Medicine–vol. 25, No. 1, Jul. 1980–T. P. Reed & R. A. Erb–pp. 25–28.

J. Reprod. Medicine–vol. 23, No. 2, Aug. 1979–T. P. Reed & R. A. Erb–pp. 65–72.

*Primary Examiner*—Ronald L. Frinks
*Attorney, Agent, or Firm*—Connolly and Hutz

[57] ABSTRACT

Polymer pads are inserted between the bones of an arthritic or damaged body joint in order to better cushion the joint bones, thus relieving pain and improving function. It is preferred to introduce the pad by injecting a liquid that cures within the joint, while traction is applied to the joint bones. Silicones or tanned proteins are useful, and may contain radiopaque additives to enable radiographic inspection during injection and/or after the pad insertion is completed.

7 Claims, No Drawings

JOINT TREATMENT

The present invention relates to the treatment of body joints, more particularly joints in which deterioration of cartilage has resulted in bone rubbing against bone.

Human beings and animals frequently suffer from joint diseases that attack the normal cartilage pads which separate the bone ends in such a joint. As a result of such arthritic processes the cartilage pads can deteriorate to the point that they no longer prevent the bone ends from contacting each other. When this happens, movement of the joint becomes painful and function is impaired.

Among the objects of the present invention is the provision of a treatment that alleviates this problem by providing novel pads that can assist or take the place of the cartilage pads.

The foregoing as well as still further objects of the present invention will be more fully understood from the following description of several of its exemplifications.

According to the present invention a bone joint having defective cartilage between the bone ends, is treated by inserting between the bone ends a cushioning pad compatible with the joint for at least a month.

A desirable pad for such insertion is an elastomeric material such as a hardened polymeric gel. Where the joint is one that is at least partially encapsulated, it is preferred to introduce the elastomeric material as a liquid, injected directly into the joint and caused to gel or harden within the joint. If there is a tear or opening in the synovial membrane surrounding the joint, the joint can be positioned to locate the tear or opening at or near the upper portion of the joint and the injection site located at a low level so that the injected liquid does not reach or flow out the tear or opening.

To make sure the injection is in the desired location, it can be made with the help of a fluoroscopic display of the joint. Also radiopaque materials such as finely divided or colloidal silver, BaSO$_4$, gold, platinum, iron or radiopaque dyes can be dispersed in the injected liquid to render it observable.

In a fully encapsulated joint it may be desirable to withdraw at least some of the synovial fluid before injecting the prosthetic-pad-forming mixture. Where substantial amounts of synovial fluid are in such joint at the time of the injection, the injection is best accomplished at a rate slow enough for the injected material to form its own stratum and not significantly mix with that fluid. Injection through a needle having a 1.5 to 2.5 millimeter wide bore can then be at a rate of about 20 cc or less per minute. Also the injection is then desirably effected with the bone ends (or bone and socket) held vertically spaced from each other as by means of a traction device, so that the injected mixture can completely cover the lower position bone end or socket and lift any free or excess synovial fluid to the higher levels of the joint. The injected liquid should then have a density greater than that of the synovial fluid. Some synovial fluid can remain below the layer of injected liquid, particularly if that fluid is absorbed in the cartilage at the bottom of the joint, but it is preferred that the fluid not mix with injected liquid.

Where the injected mixture contains more than about 2% by weight of finely divided metal dispersed in it, it tends to be more viscous and require a larger needle bore or even a trocar, for injection.

The pad-forming liquid can be injected to half fill a joint capsule, inasmuch as the resulting pad will still not seriously restrict joint mobility. A pad that completely fills the joint capsule may sometimes be desirable even though it significantly limits the mobility of the joint. The pad thickness between the joint bones should be at least about 2 millimeters throughout.

The usual asepsis is observed during the injection. Care should be taken however not to make a final rinse of the syringe or needle interior with anything that can cause premature gelling of the gel-forming liquid before it discharges from the needle.

Where the liquid being injected is too viscous, it can also be introduced into the joint throughout an arthroscope or the like inasmuch as such instruments provide passageways as much a five millimeters wide through the joint capsule, and permit visual inspection of the capsule interiors.

One desirable liquid that can be injected into a joint for the purpose of the present invention is a silicone that gels and hardens to a rubbery solid on standing or when heated to temperatures as high as body temperature, with or without a catalyst. The silicones described in U.S. Pat. No. 4,245,623 and in the related Erb et al papers on pages 65–72 of the August 1979 issue of the Journal of Reproductive Medicine, are particularly suitable because they have been formulated for compatability with body tissue. Also they incorporate very finely divided silver, minus 400 mesh, which renders the silicone formulation radiopaque and also greatly increases its density.

Other silicone formulations that cure at low or room temperatures, are described in U.S. Pat. Nos. 2,979,420, 3,647,917, 3,296,195, 3,296,191 and 4,301,269, and can also be general medical grade formulations of liquid diorgano polysiloxanes containing methyl and vinyl radicals with an organosilicon compound containing silicon-bonded hydrogen and a platinum catalyst.

Where the liquid to be introduced is a mixture that spontaneously hardens, it generally has a working time of at least a few minutes before it gels, and this allows for its injection. By limiting the amount of catalyst present in such a mixture, its working time can be increased to as much as 100 minutes if desired, and the extra working time can be used to remove any air bubbles introduced into the mixture when it is being mixed. It is not essential to remove all air bubbles before injection.

Some room-temperature-curing silicone formulations generate acetic acid as they cure, and these can also be used for the present invention inasmuch as the total quantity of silicone injected is fairly small and the acetic acid is rapidly neutralized by the surrounding tissue. Propanol can also be generated by some silicone polymerizations, and that too is well tolerated.

Where the lowest viscosity is desired for the formulation being injected, it can be prepared with less of the colloidal silica generally present in commercial silicone formulations, even though this reduces the toughness of the polymerized product. Also, as shown in the Erb papers, the polymerizable silicone can be diluted with a non-reactive or end-blocked silicone such as Dow-Corning 360 Medical Fluid which has a viscosity of only about 20 centistokes. Non-reactive dimethyl silicone oligomers having viscosities of 10 centistokes are also suitable diluents.

A very effective formulation for injection, as described by Erb, is a mixture of, by weight:

68 parts polymerizable silicone containing 23% silica filler
17 parts inactive silicone diluent
15 parts silver powder to which is added stannous octoate catalyst in an amount 1% by weight of polymerizable silicone ingredient. That ingredient is a mixture of OH-capped dimethyl silicone with an equivalent amount of propyl orthosilicate.

The formulations should be sterilized before they are injected, and this is best accomplished by heating. Minimum heating times and temperatures are preferred inasmuch as excessive heating prolongs the subsequent curing time. When a catalyst is used it is sterilized separately before it is added to the formulation.

The foregoing injections can also be made in all joints, for example in the metatarsal, shoulder, knee, ankle or hip joints, and even in joints such as those between the vertebrae of the backbone, which are not encapsulated but which are closely surrounded by tendons and other tissues. In the last-mentioned joints it is preferred to have the injection liquid of relatively high viscosity so that it does not spread very far from the injection site.

Some joints are damaged as by trauma without significant injury to, or deterioration of, their cartilage cushions. Thus a knee joint can have a lateral tendon torn, permitting undesired lateral joint flexure. The injection of a pad thick enough to cap both the tibial and femoral bone ends will then help keep the joint motion from too much lateral play.

After the injection is completed, the joint is maintained in traction until the desired curing is completed. The injection equipment can then be withdrawn, and if necessary the puncture site stitched to close it, and suitably dressed.

Other hardened polymeric gels made from body-compatible proteins such as gelatin can be used in accordance with the present invention. Thus powdered gelatin can be dissolved in a little hot water, the resulting solution mixture with a tanning composition such as powdered tannin or a concentrated solution of tannin and glycerine in water, with or without a little formaldehyde, and the final composition adjusted to about body temperature are injected. The tanning action takes some time to complete so that, by adding the tanning agent after all other ingredients are dissolved, the final composition will remain sufficiently fluid and injectable for a few minutes. It then hardens to a rubbery solid.

A mixture of about 6 grams powdered gelatin, 15 cc water, 15 cc glycerine and 1.8 grams tannin, will in this way produce a tanned produce that will require sixty pounds of force to be penetrated by a wood plunger having a ¾ inch by ¾ inch cross-section. The addition of a little formaldehyde to the foregoing formulation makes a tanned product that is even tougher. If the mixture is completely tanned before injection, it is best heated to about 110° F. to melt it and to effect its injection with an arthroscope or trocar.

Other suitable gelatin formulations are described in U.S. Pat. No. 4,292,972, but the aeration and foaming of that patent is not needed. Radiopaque additions can be made to any protein formulation.

Gelatin hardened by any of the above techniques tends to be absorbed by the body after some period of time, but the more tanned the gelatin the slower is its rate of absorption. The foregoing tanned gelatin will remain in a joint at least about one month.

The hardened gels of the present invention can alternatively be prepared outside the body, pre-molded into the shape of a cap for a bone end, and fitted in place through a slit made surgically in the wall of the joint capsule. A rubbery molded cap can have a wall thickness of about 1/16 to about ⅛ inch and can be fitted through a slit only about ⅝ inch long. When prepared outside the body, these hardened materials can be made by techniques not possible otherwise. Thus they can be heat-cured at elevated temperatures and polymerized from reactants that are not tolerated by body tissues. Polyurethane resins can for example be prepared from isocyanates which are not tolerated, to yield a polymer that is tolerated by body tissues.

Pre-molding of a rubbery cap is best accomplished after the bone that is to receive the cap is measured and the cap is molded to fit. Thus X-ray photographs of the bone end can be taken, and a cap-forming mold shaped from plastic clay or the like to approximately correspond to the bone end. The final cap should be molded with a margin that extends around the bone end enough to help hold the cap in place in the joint. If desired, one or more perforations can be made through the cartilage-engaging portion of the cap to permit the passage of synovial fluid.

In some cases a joint should be surgically opened as for instance to remove detached cartilage fragments or even bone spurs or spicules or the like. A number of differently shaped bone caps can be prepared beforehand, and the closest cap fitted with the joint in traction, after which the traction can be discontinued and the joint closed.

Alternatively the opened joint, after cleaning and while under traction, can have the gellable liquid poured in and that liquid then permitted to gel in place. The cleaned joint can be positioned with its bones extending horizontally, in which event the joint capsule can be essentially filled by the gellable liquid, or with the bones extending vertically in which event the gellable liquid fills only the lower portion of the joint.

Removal of cartilage fragments and bone spicules can sometimes be effected with the help of an arthroscope and without fully opening a joint. In such a situation the gellable liquid can also be introduced through the arthroscope.

The presence in a diseased joint of a metabolite such as gelatin, changes the course of the disease and slows down the deterioration, whether the metabolite is in the form of a pad, or is merely injected without hardening. While the tanning of such gelatin extends its metabolic absorption time, the untanned gelatin is also helpful in slowing the cartilage degeneration rate of an arthritic joint. At least about 30 milligrams of gelatin for each square centimeter of all the cartilage in the joint, should be injected for this purpose. Such injections can be repeated every month so long as they are helpful. The injection of gelatin so heavily tanned as to solidify in a joint, can be repeated every two months. The presence of excess hardener or tanning agent in the joint, as for example in the above-noted gelatin-water-glycerine-tannin mixture, also tends to further retard cartilage degeneration.

The gelatin used according to the present invention can be obtained from the hydrolysis of animal bone or skin, and should be of U.S.P grade. It need not have the purity of photographic grade gelatin.

Some hardened proteins such as the foregoing tanned gelatin formulation, tend to be sticky at body temperatures and thus tend to adhere to the bones in the joint. If it is desired to have the joint so treated fully mobile, one or both of the sticky pad faces can be treated with concentrated formaldehyde solution in water to further harden that face.

Alternatively the sticky-faced pad can be prepared as a laminate by sandwiching two thin sticky-faced pad layers to the opposite faces of a juxtaposed pair of polyethylene films. These films will easily slide with respect to each other so that the sticky pad halves they carry can remain adhered to their respective bones without significant loss of joint mobility.

The joint treatments of the present invention are best combined with other treatments that help combat the specific joint disorder being treated. Thus the administration of anti-arthritic medication such as steroids, non-steroidal anti-inflammatory drugs such as aspirin, indomethacin, gold injections, etc. can be made in the usual manner and combined with the implant or the injection of the present invention. Indomethacin is also a good hardener for gelatin.

The hardened gelatins can also be used as protective coverings for burns, particularly after the burnt skin is removed. They can be first melted, sterilized dry or with steam, then cooled to about 110° F. and poured or buttered over the burnt tissues. The coating so applied will then cool further and harden sufficiently to provide a good barrier against infectious agents. It is also well tolerated by the body. In the event the exposed surface of the coating is too sticky, it can be hardened as above noted, or covered with surgical gauze.

Should it be desired to remove the coating, as for example to apply skin grafts, the coating can be melted and washed away by the application of a stream of water heated to about 110° F.

The hardened gelatins are of rubbery nature and tolerated well enough to be suitable for patching or covering body wounds, both internal and external. Because of their sticky character at body temperature, they adhere to body membranes and help reduce oozing from abraded, burnt, or injured surfaces One or more antibiotics can be dispersed in the mixture to be injected, but they are not needed. The specific antibiotic or antibiotics selected for this purpose are those to which the body shows no adverse reaction.

The traction used to hold joint bones separated, can be replaced by or combined with a spacer that is inserted between the bones when the joint is surgically opened. The spacer can be provided with a tail by which it can be grasped to pull it out after a pad is inserted or after a pad is formed by gelling.

What is claimed:

1. The treatment of a bone joint having defective cartilage between the bone ends, which treatment is characterized by the insertion between the bone ends of a cushioning gel of hardened gelatin compatible with the joint.

2. The treatment of a bone joint having defective cartilage between the bone ends, which treatment is characterized by the injecting into the joint without surgery, a liquid that is subsequently converted into a cushioning pad between the bone ends.

3. The treatment of claim 2 in which the liquid injected is radiopaque and the injecting is fluoroscopically monitored.

4. The treatment of claim 2 in which the bone joint is an encapsulated joint and the injecting is effected while the bone ends are separated from each other, and the bone ends are kept separated until the liquid is converted to the pad.

5. The treatment of claim 1 in which the cushioning pad is a hardened polymeric gel.

6. The treatment of claim 5 in which the hardened polymeric gel is a silicone.

7. The treatment of claim 5 in which the hardened polymeric gel is a gel of hardened gelatin.

* * * * *